US009334297B2

(12) United States Patent
Scheidt et al.

(10) Patent No.: US 9,334,297 B2
(45) Date of Patent: May 10, 2016

(54) CHIRAL IMIDAZOLIUM SALTS FOR ASYMMETRIC CATALYSIS

(71) Applicant: Northwestern University, Evanston, IL (US)

(72) Inventors: Karl A. Scheidt, Evanston, IL (US); Christopher T. Check, Evanston, IL (US); Kipo P. Jang, Yongin-si (KR)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/854,950

(22) Filed: Sep. 15, 2015

(65) Prior Publication Data

US 2016/0075728 A1     Mar. 17, 2016

Related U.S. Application Data

(60) Provisional application No. 62/050,565, filed on Sep. 15, 2014.

(51) Int. Cl.
| | |
|---|---|
| *C07F 15/02* | (2006.01) |
| *B01J 31/12* | (2006.01) |
| *C07D 307/33* | (2006.01) |
| *C07F 7/18* | (2006.01) |
| *C07F 5/04* | (2006.01) |
| *B01J 31/22* | (2006.01) |

(52) U.S. Cl.
CPC .................. *C07F 15/02* (2013.01); *B01J 31/22* (2013.01); *C07D 307/33* (2013.01); *C07F 5/04* (2013.01); *C07F 7/188* (2013.01); *B01J 2231/323* (2013.01); *B01J 2531/842* (2013.01)

(58) Field of Classification Search
USPC ............................................ 546/10; 502/155
See application file for complete search history.

(56) References Cited

PUBLICATIONS

Luo, Y. et al., "Enantioselective Synthesis of Allylboronates and Allylic Alcohols by Copper-Catalyzed 1,6-Boration", Angew Chem Int Ed Engl 2014, 53, 4186-4190.
Hirsch-Weil, D. et al., "Isoquinoline-based chiral monodentate N-heterocyclic carbenes", Chem. Comm. 2010, 46, 7525-7527.
O'Brien, J. M. et al., "Enantioselective Synthesis of Boron-Substituted Quaternary Carbons by NHC-Cu-Catalyzed Boronate Conjugate Additions to Unsaturated Carboxylic Esters, Ketones, or Thioesters", J. Am. Chem. Soc. 2010, 132, 10630-10633.
Citadelle, C. A. et al., "Simple and versatile synthesis of copper and silver N-heterocyclic carbene complexes in water or organic solvents", Dalton Trans. 2010, 39, 4489-4491.
Pangborn, A. B. et al., "Safe and Convenient Procedure for Solvent Purification", Organometallics 1996, 15, 1518.
Rios, R. et al., "Synthesis, resolution and crystallographic characterization of a new C2-symmetric planar-chiral bipyridine ligand: application to the catalytic enantioselective cyclopropanation of olefins", Chem. Comm., 2000, 377.
Ruble, J. C. et al., "Chiral δ- -Complexes of Heterocycles with Transition Metals: A Versatile New Family of Nucleophilic Catalysts", J. Org. Chem. 1996, 61, 7230.
Lee, J.-E. et al., "Catalytic Asymmetric Boration of Acyclic a,b-Unsaturated Esters and Nitriles", Angew. Chem. 2008, 120, 151.
Infante, R. et al., "Enantioselective One-Pot Catalytic Synthesis of 4,5-Epoxy-3-alkanols and 1-Phenyl-2,3-epoxy-1-alkanols from α,β-Unsaturated Aldehydes", Eur. J. Org. Chem. 2013, 2013, 4863.
Phillips, E. et al., "N-Heterocyclic Carbene-Catalyzed Conjugate Additions of Alcohols", J. Am. Chem. Soc., 2010, 132, 13179-13181.
Enders, D. et al., "Organocatalysis by N-Heterocyclic Carbenes", Chem. Rev. 2007, 107, 5606-5655.
Herrmann, W., "N-Heterocyclic Carbenes: A New Concept in Organometallic Catalysis", Agnew. Chem. Int. Ed., 2002, 41, 1290-1309.
Arduengo, A., "Looking for Stable Carbenes: The Difficulty in Starting Anew", Accounts of Chemical Research, 32, 11, 1999.
Cesar, V. et al., "Chiral N-heterocyclic carbenes as stereodirecting ligands in asymmetric catalysis", Chem. Soc. Rev. 2004, 33, 619-636.
Marion, N. et al., "N-Heterocyclic Carbenes as Organocatalysts", Angew. Chem., Int. Ed. 2007, 46, 2988-3000.
Hahn, F. E. et al., "Heterocyclic Carbenes: Synthesis and Coordination Chemistry", Angew. Chem., Int. Ed. 2008, 47, 3122-3172.
Bugaut, X. et al., "Organocatalytic umpolung: N-heterocyclic carbenes and beyond", Chem. Soc. Rev. 2012, 41, 3511-3522.
Cohen, D. T. et al., "Cooperative Lewis acid/N-heterocyclic carbene catalysis", Chem. Sci. 2012, 3, 53-57.
Douglas, J. et al., NHCs in Asymmetric Organocatalysis: Recent Advances in Azolium Enolate Generation and Reactivity, Synthesis 2012, 44, 2295-2309.
Vora, H. U. et al., "Exploiting Acyl and Enol Azolium Intermediates via N-Heterocyclic Carbene-Catalyzed Reactions of a-Reducible Aldehydes", Adv. Synth. Catal. 2012, 354, 1617-1639.
De Sarkar, S. et al., "Catalysis with N-Heterocyclic Carbenes under Oxidative Conditions", Chem. Eur. J. 2013, 19, 4664-4678.
Ryan, S. J. et al., "Acyl anion free N-heterocyclic carbene organocatalysis", Chem. Soc. Rev. 2013, 42, 4906-4917.
Candish, L. et al., "N-heterocyclic carbene cascade catalysis: Dual Brønsted/Lewis base rearrangement of cyclopropyl enol esters to dihydropyranones", Chem. Sci. 2012, 3, 380-383.
Chen, J., et al. "Asymmetric catalysis with N-heterocyclic carbenes as non-covalent chiral templates" Nat. Commun. 2014, 5.
Arduengo, A. J. et al., "Electronic Stabilization of Nucleophilic Carbenes", J. Am. Chem. Soc. 1992, 114, 5530-5534.
Bolm, C. et al., "The First Planar-Chiral Stable Carbene and Its Metal Complexes", Organometallics, 2002, 21, 707-710.
Broggini, D. et al., "Synthesis and Structure of an Enantiomerically Pure C2 Symmetric Ferrocenyl Carbene", Helv. Chim. Acta 2002, 85, 2518-2522.

(Continued)

*Primary Examiner* — Charanjit Aulakh
(74) *Attorney, Agent, or Firm* — Reinhart Boerner Van Deuren s.c.

(57) ABSTRACT

Planar chiral N-heterocyclic carbenes that incorporate an iron sandwich complex into the NHC framework are disclosed for use in organocatalytic and transition metal-catalyzed reactions.

8 Claims, 2 Drawing Sheets

(56) References Cited

PUBLICATIONS

Perry, M. C. et al., Chiral N-heterocyclic carbene-transition metal complexes in asymmetric catalysisTetrahedron: Asymmetry 2003, 14, 951-961.

Seo, H. et al., "Synthesis of P- and S-Functionalized Chiral Imidazolium Salts and Their Rh and Ir Complexes", Organometallics, 2003, 22, 618-620.

Fürstner, A. et al., "Effective Modulation of the Donor Properties of N-Heterocyclic Carbene Ligands by "Through-Space" Communication within a Planar Chiral Scaffold", J. Am. Chem. Soc. 2007, 129, 12676-12677.

Matsuoka, Y. et al., "Cyclophane-Type Imidazolium Salts with Planar Chirality as a New Class of N-Heterocyclic Carbene Precursors", Chem. Eur. J. 2008, 14, 9215-9222.

Struble, J. R. et al., "Synthesis of an N-Mesityl Substituted Chiral Imidazolium Salt for NHC-Catalyzed Reactions", Org. Lett. 2008, 10, 957-960.

Würtz, S. et al., "IBiox[(−)-menthyl]: A Sterically Demanding Chiral NHC Ligand", J. Am. Chem. Soc. 2009, 131, 8344-8345.

Ma, Q. et al., "Planar chiral imidazolium salts based on [2.2]paracyclophane in the asymmetric rhodium-catalyzed 1,2-addition of arylboronic acids to aldehydes", Tetrahedron: Asymmetry 2010, 21, 292-298.

Herrmann, W. A. et al., "Chiral Heterocylic Carbenes in Asymmetric Homogeneous Catalysis", Angew. Chem., Int. Ed. 1996, 35, 2805-2807.

Herrmann, W. A. et al., "Metal Complexes of Chiral Imidazolin-2-ylidene Ligands", Organometallics 1997, 16, 2472-2477.

Bolm, C. et al., "Planar chiral arene chromium(0) complexes: potential ligands for asymmetric catalysis", Chem. Soc. Rev. 1999, 28, 51-59.

Matsushima, Y. et al., "Asymmetric Catalysis of Planar-Chiral Cyclopentadienylruthenium Complexes in Allylic Amination and Alkylation", J. Am. Chem. Soc. 2001, 123, 10405-10406.

Gibson, S. E. et al., "[2.2]Paracyclophane derivatives in asymmetric catalysis", Org. Biomol. Chem. 2003, 1, 1256-1269.

Halterman, R. L., "Synthesis and Applications of Chiral Cyciopentadienyimetal Complexes" Chem. Rev. 1992, 92, 965-994.

Togni, A. "Planar-Chiral Ferrocenes: Synthetic Methods and Applications", Angew. Chem., Int. Ed. 1996, 35, 1475-1477.

Richards, C. J. et al., "Recent advances in the generation of non-racemic ferrocene derivatives and their application to asymmetric synthesis", Tetrahedron: Asymmetry 1998, 9, 2377-2407.

Colacot, T. J., "A Concise Update on the Applications of Chiral Ferrocenyl Phosphines in Homogeneous Catalysis Leading to Organic Synthesis", Chem. Rev. 2003, 103, 3101-3118.

Fu, G. C., "Asymmetric Catalysis with "Planar-Chiral" Derivatives of 4-(Dimethylamino)pyridine", Acc. Chem. Res. 2004, 37, 542-547.

Gómez Arrayás, R. et al., "Recent Applications of Chiral Ferrocene Ligands in Asymmetric Catalysis", Angew. Chem., Int. Ed. 2006, 45, 7674-7715.

Schiffner, J. A. et al., "Enantioselective Conjugate Borylation", Angew. Chem., Int. Ed. 2010, 49, 1194-1196.

Hutt, J. T. et al., "Efficient, Single-Step Access to Imidazo[1,5-a]pyridine N-Heterocyclic Carbene Precursors", Org. Lett. 2011, 13, 5256-5259.

Chan, A. et al., "Highly Stereoselective Formal [3+3] Cycloaddition of Enals and Azomethine Imines Catalyzed by N-Heterocyclic Carbenes", J. Am. Chem. Soc. 2007, 129, 5334-5335.

Phillips, E. M. et al., "Highly Diastereo- and Enantioselective Additions of Homoenolates to Nitrones Catalyzed by N-Heterocyclic Carbenes", J. Am. Chem. Soc. 2008, 130, 2416-2417.

Kawanaka, Y. et al., "N-Heterocyclic Carbene-Catalyzed Enantioselective Mannich Reactions with r-Aryloxyacetaldehydes", J. Am. Chem. Soc. 2009, 131, 18028-18029.

Raup, D. E. A. et al., "Cooperative catalysis by carbenes and Lewis acids in a highly stereoselective route to y-lactams", Nat Chem 2010, 2, 766-771.

Cohen, D. T. et al., "Catalytic Dynamic Kinetic Resolutions with N-Heterocyclic Carbenes: Asymmetric Synthesis of Highly Substituted b-Lactones", Angew. Chem., Int. Ed. 2012, 51, 7309-7313.

Dugal-Tessier, J. et al., "An N-Heterocyclic Carbene/Lewis Acid Strategy for the Stereoselective Synthesis of Spirooxindole Lactones", Angew. Chem., Int. Ed. 2012, 51, 4963-4967.

Burstein, C. et al., "N-Heterocyclic Carbene-Catalyzed Conjugate Umpolung for the Synthesis of y-Butyrolactones", Synthesis 2006, 2006, 2418-2439.

Li, Y. et al., "Stereoselective Synthesis of y-Butyrolactones via Organocatalytic Annulations of Enals and Keto Esters", Adv. Synth. Catal. 2008, 350, 1885-1890.

Mahatthananchai, J. et al., "The effect of the N-mesityl group in NHC-catalyzed reactions", Chem. Sci. 2012, 3, 192-197.

Chaulagain, M. R. et al., "New N-Heterocyclic Carbene Ligand and Its Application in Asymmetric Nickel-Catalyzed Aldehyde/Alkyne Reductive Couplings", J. Am. Chem. Soc. 2007, 129, 9568-9569.

Liu, P. et al., "Ligand Steric Contours to Understand the Effects of N-Heterocyclic Carbene Ligands on the Reversal of Regioselectivity in Ni-Catalyzed Reductive Couplings of Alkynes and Aldehydes", J. Am. Chem. Soc. 2011, 133, 6956-6959.

Seiders, T. J. et al., "Enantioselective Ruthenium-Catalyzed Ring-Closing Metathesis", Org. Lett. 2001, 3, 3225-3228.

Miller, K. M. et al., "Catalytic Asymmetric Reductive Coupling of Alkynes and Aldehydes: Enantioselective Synthesis of Allylic Alcohols and a-Hydroxy Ketones", J. Am. Chem. Soc. 2003, 125, 3442-3443.

Ito, H. et al., "Boration of an a,b-enone using a diboron promoted by a copper(I)-phosphine mixture catalyst", Tetrahedron Lett. 2000, 41, 6821-6825.

CHIRAL IMIDAZOLIUM SALTS FOR ASYMMETRIC CATALYSIS

This application claims priority to and the benefit of application Ser. No. 62/050,565 filed Sep. 15, 2014—the entirety of which is incorporated herein by reference.

This invention was made with government support under CHE1152010 awarded by the National Science Foundation. The government has certain rights in the invention.

FIELD OF THE INVENTION

The present invention relates to a class of rigid, planar chiral N-heterocyclic carbene catalysts that incorporate a sterically demanding iron sandwich complex.

BACKGROUND OF THE INVENTION

N-Heterocyclic carbenes (NHCs) are unique and enabling ligands for transition metal (TM) catalysis and have emerged as selective organocatalysts for a remarkably diverse array of transformations (Arduengo, A. J., *Acc. Chem. Res.* 1999, 32, 913-921; Herrmann, W. A., *Angew. Chem., Int. Ed.* 2002, 41, 1290-1309; Cesar, V. et al., *Chem. Soc. Rev.* 2004, 33, 619-636; Marion, N. et al., *Angew. Chem., Int. Ed.* 2007, 46, 2988-3000; Hahn, F. E. et al., *Angew. Chem., Int. Ed.* 2008, 47, 3122-3172; Enders, D. et al., *Chem. Rev.* 2007, 107, 5606-5655; Bugaut, X. et al., *Chem. Soc. Rev.* 2012, 41, 3511-3522; Cohen, D. T. et al., *Chem. Sci.* 2012, 3, 53-57; Douglas, J. et al., *Synthesis* 2012, 44, 2295-2309; Vora, H. U. et al., *Adv. Synth. Catal.* 2012, 354, 1617-1639; De Sarkar, S. et al., *Chem. Eur. J.* 2013, 19, 4664-4678; Ryan, S. J. et al., *Chem. Soc. Rev.* 2013, 42, 4906-4917; Phillips, E. M. et al., *J. Am. Chem. Soc.* 2010, 132, 13179-13181; Candish, L. et al., *Chem. Sci.* 2012, 3, 380-383; Chen, J.; Huang, Y. *Nat. Commun.* 2014, 5). Given the importance of these strongly nucleophilic Lewis bases in chemistry, major efforts by many investigators have produced numerous classes of structurally and electronically diverse N-heterocyclic carbenes. Within this truly broad family of heteroatom-stabilized divalent carbon species, two major classes of N-heterocyclic carbenes derived from triaziolium and imidazolium salts have demonstrated applicability as ligands for transition metal and Lewis base catalysis. Traizolium salts have seen broad application in asymmetric organocatalysis, but their success in metal-based transformations has been limited. In contrast, imidazolium-derived N-heterocyclic carbenes (imidazol-2-ylidenes) have been widely deployed as successful ligands for transition metal catalysis and are unique catalysts for organocatalytic transformations. The imidazol-2-ylidene, IMes, was first introduced by Arduengo in 1992 (Arduengo, A. J. et al., M. *J. Am. Chem. Soc.* 1992, 114, 5530-5534. Surprisingly, since the disclosure of this important species over two decades ago there still remain few chiral scaffolds based on IMes (Bolm, C. et al., *Organometallics* 2002, 21, 707-710; Broggini, D. et al., *Helv. Chim. Acta* 2002, 85, 2518-2522; Perry, M. C. et al., *Tetrahedron: Asymmetry* 2003, 14, 951-961; Seo, H.; Park, H.-j.; Kim, B. Y. et al., *Organometallics* 2003, 22, 618-620; Fürstner, A. et al., *J. Am. Chem. Soc.* 2007, 129, 12676-12677; Matsuoka, Y. et al., *Chem. Eur. J.* 2008, 14, 9215-9222; Struble, J. R. et al., *Org. Lett.* 2008, 10, 957-960; Würtz, S. et al., *J. Am. Chem. Soc.* 2009, 131, 8344-8345; Ma, Q. et al., *Tetrahedron: Asymmetry* 2010, 21, 292-298). The saturated analog of IMes (4,5-Dihydro-1,3-dimesityl-1H-imidazolium, SIMes) has been translated into multiple chiral variants. Although these chiral SIMes N-heterocyclic carbenes have been successful in transition metal catalysis, their reactivity in organocatalysis is markedly different from IMes and have only recently been employed in asymmetric transformations.

A major challenge in carbene catalysis is the design and implementation of a chiral IMes analog with competent ligand and/or catalyst characteristics. While $C_2$-symmetric chiral imidazoliums are presumably the most accessible through the dimerization of stereodefined amines, these N-heterocyclic carbenes often deliver low levels of selectivity as ligands in transition metal catalysis and are typically unsuitable as organocatalysts (Herrmann, W. A. et al., *Angew. Chem., Int. Ed.* 1996, 35, 2805-2807; Herrmann, W. A. et al., *Organometallics* 1997, 16, 2472-2477). Most notably, structurally rigid N-heterocyclic carbenes that invoke planar chirality are scarce in the literature, with most contemporary examples featuring pendant planar chiral motifs with varying degrees of free rotation.

The success of planar chiral ligands and catalysts in asymmetric catalysis led to creating a new class of structurally rigid planar chiral N-heterocyclic carbenes (Bolm, C. et al., *Chem. Soc. Rev.* 1999, 28, 51-59; Matsushima, Y. et al., *J. Am. Chem. Soc.* 2001, 123, 10405-10406; Gibson, S. E. et al., *Org. Biomol. Chem.* 2003, 1, 1256-1269). Ferrocenyl-based motifs have arguably received the most attention as planar chiral scaffolds due to their successful application in imparting high levels of selectivity in asymmetric catalysis (Halterman, R. L. *Chem. Rev.* 1992, 92, 965-994; Togni, A. *Angew. Chem., Int. Ed.* 1996, 35, 1475-1477; Richards, C. J. et al., *Tetrahedron: Asymmetry* 1998, 9, 2377-2407; Colacot, T. J. *Chem. Rev.* 2003, 103, 3101-3118; Fu, G. C. *Acc. Chem. Res.* 2004, 37, 542-547; Gómez Arrayás, R. et al., *Angew. Chem., Int. Ed.* 2006, 45, 7674-7715). Encouraged by the high levels of facial selectivity conferred by these scaffolds, it is desirable to create a N-heterocyclic carbene featuring fusion of a metal sandwich complex with the core structure of an N-heterocyclic carbene framework.

SUMMARY OF THE INVENTION

The present invention can be directed to a rigid planar chiral N-heterocyclic carbene (NHC) catalyst which can incorporate a sterically demanding iron sandwich complex. The NHC catalyst can comprise, without limitation, an imidazolium salt component. In certain embodiments, the fusion of an azolium motif with a ferrocenyl core provides a tunable and modular approach for a chiral environment around the C-2 position.

Without limitation, this invention can be directed to a rigid planar chiral NHC catalyst, such as an imidazolium catalyst, for use in asymmetric organocatalysis and transition metal catalysis (see, e.g., Scheme 1, in accordance with certain non-limiting embodiments of this invention).

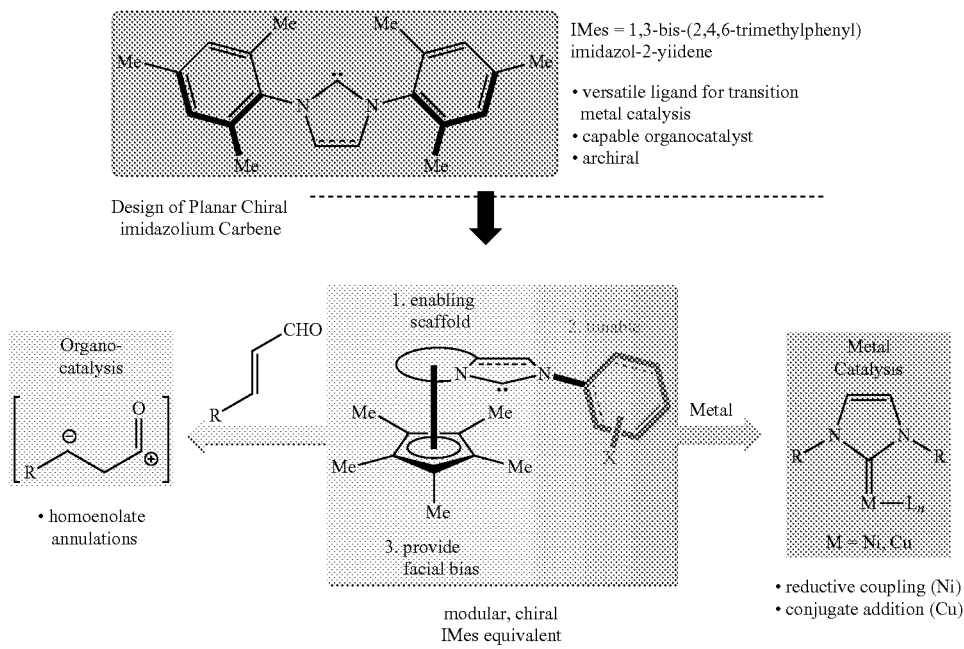

Scheme 1

Other objectives, features, benefits and advantages of the present invention will be apparent from this summary and its descriptions of certain embodiments of such NHC catalysts, and will be readily apparent to those skilled in the art having knowledge of the synthetic techniques described therewith. Such objectives, features, benefits and advantages will be apparent from the above as taken into conjunction with the accompanying examples, data, figures and all reasonable inferences to be drawn therefrom.

DETAILED DESCRIPTION OF CERTAIN EMBODIMENTS

The invention relates to a rigid planar chiral N-heterocyclic carbene (NHC) catalyst which incorporates a sterically demanding iron sandwich complex. The catalyst comprises a NHC component and an iron complex component. The NHC component can be, for example, an imidazolium. The iron complex can be, for example, ferrocene (or a ferrocenyl component). The NHC component can also be substituted. For example, an imidazolium component can be substituted at the free nitrogen position with, for example, certain aryl groups (Ar). Various non-limiting examples of aryl groups are recited below in Scheme 2 below. Synthesis of the NHC as disclosed herein starts with known iron-sandwich complex 1, which can easily be prepared on multi-gram scale in six synthetic steps (Scheme 2) (Rios, R.; Liang, J.; Lo, M. M. C.; Fu, G. C. *Chem. Comm.* 2000, 377-378, incorporated herein by reference).

Scheme 2

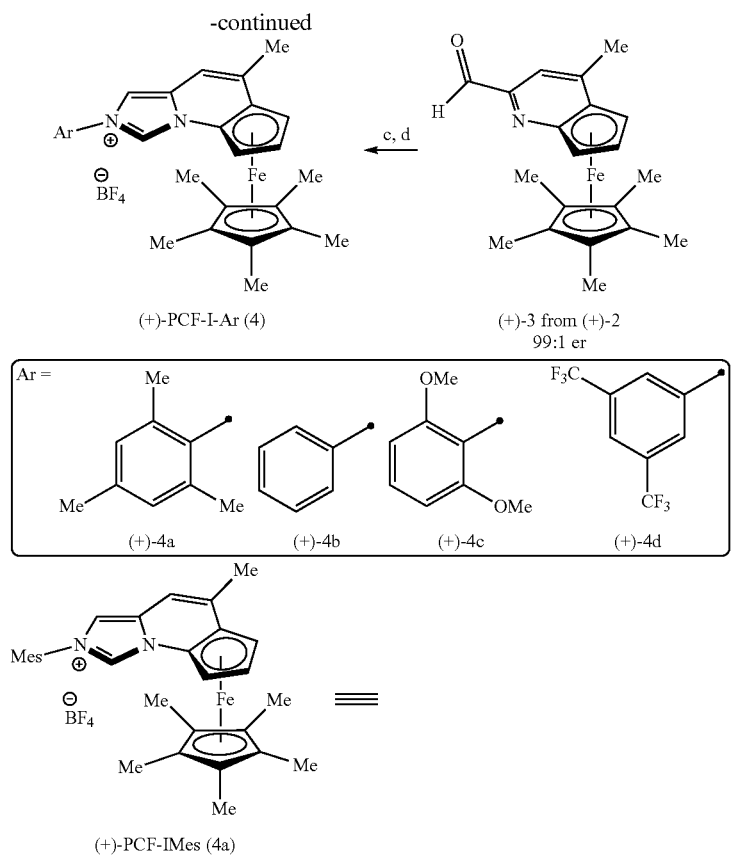

*a*Conditions: (a) Pd(dppf)Cl₂, NaOAc, (+)-pseudoephedrine, toluene, CO (balloon), 61% (combined yield of diastereomers); (b) DIBAL-H, THF, 78%; (c) Ar—NH₂, formaldehyde, EtOH (HCl), THF, 51-70%; (d) AgBF₄, MeCN, 74-95%.

Referring to Scheme 2, the preparation of enantiopure aldehyde 3 involves the use of chiral preparative high-performance liquid chromatography (HPLC), however a diastereomeric separation is advantageous for larger scale preparations. After multiple attempts invoking a variety of diastereomeric separation methods, pseudoephedrine amides (+)-2 and (−)-2 are easily separated by column chromatography. Palladium-catalyzed aminocarbonylation of aryl chloride 1 allows for a straightforward route to the pseudo-ephedrine amide (2) and enables the crucial resolution. Subsequent reductive cleavage of the amide with diisobutylaluminium hydride (DIBAL-H) yields the enantiopure aldehyde (>99:1 er by HPLC). Formation of the planar chiral NHCs is then achieved through an annulation described by Aron and coworkers with the corresponding aniline and formaldehyde, followed by anion exchange with AgBF₄ (Hutt, J. T. et al., *Org. Lett.* 2011, 13, 5256-5259). Absolute configuration of the catalysts was then determined by X-ray crystal analysis.

Figure 1:
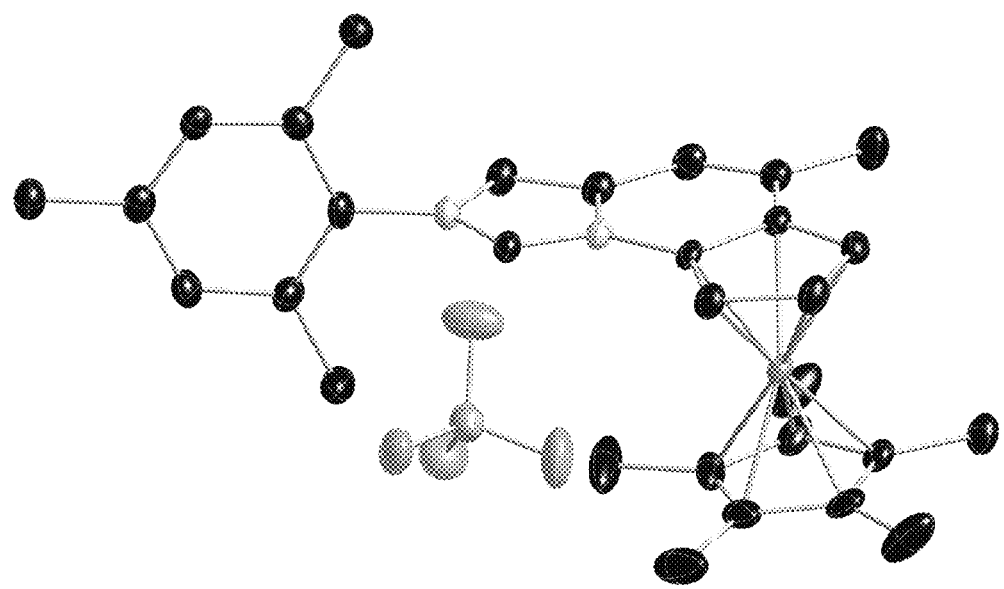
FIG. 1 is the structure of (4a).

With an optimal route to the enantiopure products, the reactivity of these new NHCs as Lewis base catalysts and ligands for transition metal catalysis is explored. In particular, the rigid NHC as described herein is tried in organocatalysis (Chan, A. et al., *J. Am. Chem. Soc.* 2007, 129, 5334-5335; Phillips, E. M. et al., *J. Am. Chem. Soc.* 2008, 130, 2416-2417; Kawanaka, Y. et al., *J. Am. Chem. Soc.* 2009, 131, 18028-18029; Raup, D. E. A. et al., *Nat Chem* 2010, 2, 766-771; Cohen, D. T. et al., *Angew. Chem., Int. Ed.* 2012, 51, 7309-7313; and Dugal-Tessier, J. et al., *Angew. Chem., Int. Ed.* 2012, 51, 4963-4967; all incorportated herein by reference). One such reaction which remains difficult to perform with high levels of selectivity is the NHC-catalyzed homoenolate (a reactive intermediate that possesses an anionic or nucleophilic carbon β to a carbonyl group or its synthetic equivalent) addition to α-ketoesters first reported by Glorious in 2006 (Burstein, C. et al., *Synthesis* 2006, 2006, 2418-2439; and Li, Y. et al., *Adv. Synth. Catal.* 2008, 350, 1885-1890, all incorporated herein by reference). Promoting this transformation using catalyst 4a (FIG. 1) is successful, providing the annulation (a new ring constructed on another molecule) product in good yield (74% yield). Upon analysis of the products by chiral HPLC, the major and minor diastereomers are obtained in yield of 66:44 and 62:38 er's, respectively (Scheme 3, equation 1). Catalysts 4b and 4d are not as good for the transformation, as the corresponding reactions progress at less than 20% conversion. This lack of reactivity observed for catalysts 4b and 4d may be due to the lack of ortho-substitution on the pendant aromatic ring, which is believed to be crucial for catalyst turnover (Mahatthananchai, J. et al., *Chem. Sci.* 2012, 3, 192-197, incorporated herein by reference). Catalyst 4c provides the highest levels of enantioselectivity (85:15 er, major), but fails to demonstrate any diastereoselectivity (1:1). While the NHCs as described herein have potential to be capable Lewis base catalysts for the promotion of homoenolate reactivity, further modulation of the aryl substituent may be necessary to impart high levels of selectivity and reactivity in transformations of this nature. Further evaluation of catalyst structure requirements and applications towards organocatalytic transformations are currently ongoing.

A recent report by Montgomery et al. demonstrates the ability of saturated imidazolium NHCs to impart high levels of enantioselectivity in nickel-catalyzed reductive couplings (Chaulagain, M. R. et al., *J. Am. Chem. Soc.* 2007, 129, 9568-9569; and Liu, P. et al., *J. Am. Chem. Soc.* 2011, 133, 6956-6959, both incorporated herein by reference), whereby a $C_2$ symmetric NHC is an efficient ligand for the coupling of simple alkynes and aldehydes (Seiders, T. J. et al., *Org. Lett.* 2001, 3, 3225-3228, incorporated herein by reference). Adequate selectivity is reported for reductive coupling of alkynes and aldehydes, but there still remains room for further improvement for the enantioselectivity of these reactions (Miller, K. M. et al., *J. Am. Chem. Soc.* 2003, 125, 3442-3443, incorporated herein by reference). As such, the NHCs as described herein are also investigated as a ligand for asymmetric catalysis. Following reaction conditions developed by Montgomery, the NHCs of the invention are shown to be competent in the Ni-catalyzed reductive coupling of benzaldehyde and 1-phenyl-1-propyne using triethylsilane as the terminal reductant (Scheme 2, equation 2). The allylic alcohol product is formed with excellent regioselectivity (>20:1) and enantiomeric ratio (about 93:7). This represents the highest selectivity to date for this transformation.

Figure 2:
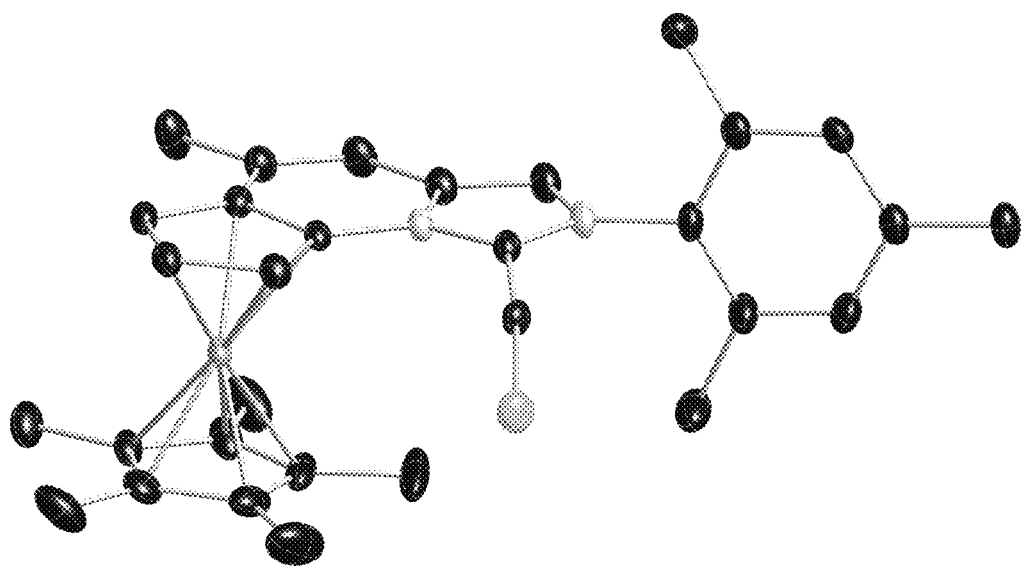
FIG. 2 is the structure of (4a-CuCl).

In another embodiment, the NHCs as described herein are used in the copper-catalyzed conjugate borylation of α,β-unsaturated esters with a boron-containing compound (Ito, H. et al., *Tetrahedron Lett.* 2000, 41, 6821-6825; Lee, J.-E. et al., *Angew. Chem., Int. Ed.* 2008, 47, 145-147; Schiffner, J. A. et al., *Angew. Chem., Int. Ed.* 2010, 49, 1194-1196; Luo, Y. et al., *Angew Chem Int Ed Engl* 2014, 53, 4186-4190; Hirsch-Weil, D. et al., *Chem. Comm.* 2010, 46, 7525-7527; and O'Brien, J. M. et al., *J. Am. Chem. Soc.* 2010, 132, 10630-10633, all incorporated herein by reference). The preparation of the enantiopure copper-NHC complex (−)-4a-CuCl is accomplished following literature procedures and a crystal structure is obtained (FIG. 2) (Citadelle, C. A. et al., *Dalton Trans.* 2010, 39, 4489-4491). This NHC-copper complex proficiently catalyzes the conjugate borylation of ethyl-cinnamate with an excellent yield (91%) and selectivity (98:2 er) (Scheme 2, equation 3).

Scheme 3

NHC-catalyzed annulation

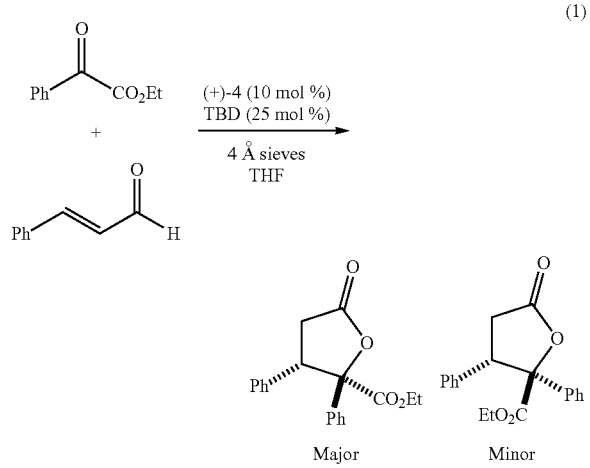

| catalyst | yield (%) | dr | er (Major) | er (Minor) |
|---|---|---|---|---|
| 4a | 74 | 1.6:1 | 66:44 er | 62:38 er |
| 4c | 62 | 1:1 | 85:15 er | 75:25 er |

Ni-NHC-catalyzed reductive coupling

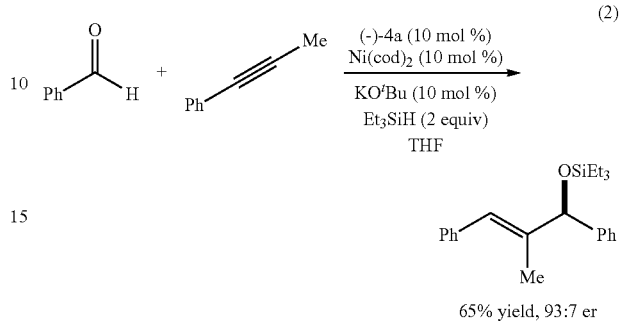

Cu-NHC-catalyzed conjugate borylation

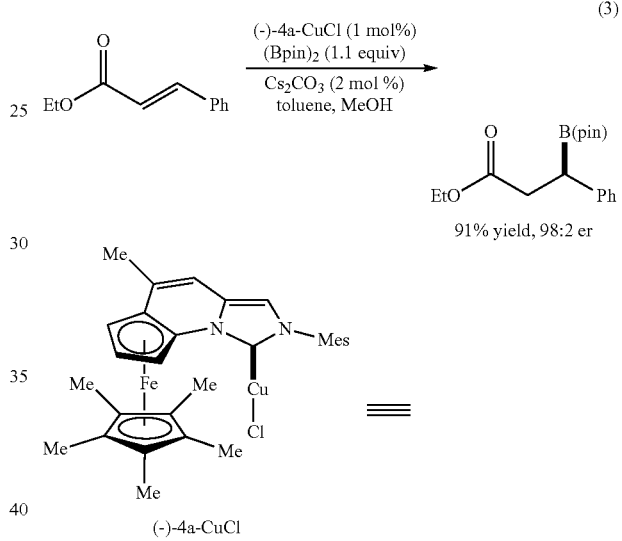

EXAMPLES OF THE INVENTION

General Information.

All reactions are carried out under a nitrogen atmosphere in oven-dried glassware with magnetic stirring. Tetrahydrofuran (THF), diethyl ether, dimethylformamide (DMF), benzene, toluene, and dichloromethane are purified by passage through a bed of activated alumina (Pangborn, A. B. et al., *Organometallics* 1996, 15, 1518, incorporated herein by reference). Reagents are purified prior to use unless otherwise stated following the guidelines of Perrin and Armarego (D. D. Perrin, W. L. Armarego, *Purification of Laboratory Chemicals;* 3rd Ed., Pergamon Press, Oxford. 1988, incorporated herein by reference). Purification of reaction products is carried out by flash chromatography using EM Reagent, Silicycle silica gel 60 (230-400 mesh) or using Sigma-Aldrich neutral, activated aluminum oxide (Brockmann I). Analytical thin layer chromatography is performed on EM Reagent 0.25 mm silica gel 60-F plates. Visualization is accomplished with UV light and ceric ammonium nitrate stain, potassium permanganate stain or ninhydrin stain followed by heating Infrared spectra are recorded on a Bruker Tensor 37 FT-IR spectrometer. $^1$H-NMR spectra are recorded on a Bruker Avance 500 MHz w/ direct cryoprobe (500 MHz) spectrometer and are reported in ppm using solvent as an internal standard. Data are reported as (ap=apparent, s=singlet, d=doublet, t=triplet, q=quartet, m=multiplet, b=broad; coupling constant(s) in Hz, integration). Proton-decoupled $^{13}$C-NMR spectra are recorded on a Bruker Avance 500 MHz w/direct cryoprobe (125 MHz) spectrometer and are reported in ppm using solvent as an internal standard (CDCl$_3$ at 77.05 ppm). Mass spectra data are obtained on a Waters Acquity Single Quadrupole ESI Spectrometer and Micromass Quadro II Spectrometer.

Synthesis of Planar Chiral Ferrocenyl NHC

Example 1

Pentamethyl-η$^5$-cyclopentadienyl (3-chloro-1-methyl-η$^5$-cyclopenta[b]pyridinyl)iron (1)

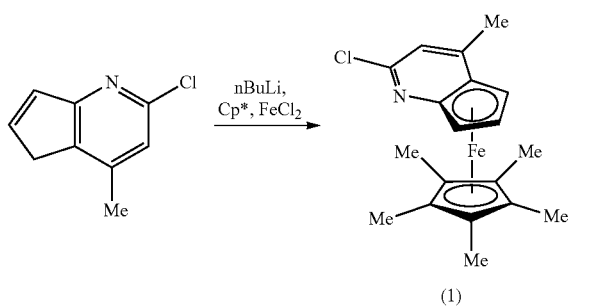

(1)

(1)—n-Butyl lithium in hexanes (1.55 M, 10.5 mL, 16.3 mmol) is added dropwise to a 0° C. solution of 1,2,3,4,5-pentamethylcyclopentadiene (2.68 mL, 16.3 mmol) in THF (70 mL), resulting in a milky-white solution. The resulting slurry is stirred for 1 hour at 0° C. and added by cannula to a slurry of iron(II) chloride (16.3 mmol) in THF (40 mL) at 0° C. (the FeCl$_2$ had been suspended in THF by heating to 40° C.). Additional portions of THF (2×10 mL) are added to completely transfer the white slurry. Upon completion of the addition, the resulting green solution is stirred at 0° C. for 1 hour and at room temperature for 1 hour. To a separate round bottom flask, n-Butyl lithium in hexanes (1.55 M, 9.15 mL, 14.2 mmol) is added dropwise to a solution of 2-chloro-4-methyl-5H-cyclopenta[b]pyridine (Rios, R.; Liang, J.; Lo, M. M. C.; Fu, G. C. *Chem. Comm.* 2000, 377; and Ruble, J. C.; Fu, G. C. *J. Org. Chem.* 1996, 61, 7230, both incorporated herein by reference) (2.35 g, 14.2 mmol) in THF (40 mL) at −78° C. and stirred for 1 hour at −78° C. and then warmed to 0° C. and stirred an additional 10 min. The solution is then transferred by cannula to the stirring solution of Cp*FeCl in THF at 0° C. After completion of the addition, the reaction mixture is allowed to slowly warmed from 0° C. to ambient temperature and stirred for 12 hours (the reaction is monitored by thin layer chromatography (TLC) analysis (20% EtOAc/Hexanes) product appears as dark purple spot). The reaction mixture is filtered through a short silica pad, rinsing with dichloromethane (DCM) and then concentrated under vacuum. The crude product is purified by flash chromatography on silica gel (5 to 10% EtOAc/Hexanes) to afford the corresponding ferrocenyl chloride (4.3 g, 12.1 mmol, 85% yield). Note: Bench stable intermediate. Analytical data for 1: $^1$H NMR (500 MHz, CDCl$_3$) δ 6.71 (d, J=1.19 Hz, 1H), 4.70 (dd, J=1.14, 2.64 Hz, 1H), 4.24 (d, J=1.14, 2.76 Hz, 1H), 3.88 (t, J=2.72 Hz, 1H), 2.39 (d, J=1.17 Hz, 3H), 1.69 (s, 15H); $^{13}$C NMR (126 MHz, CDCl$_3$) δ 154.83, 149.26, 116.54, 108.45, 80.81, 79.13, 76.57, 67.43, 62.08, 19.43, 10.17. IR (neat) ν 2905, 1699, 1653, 1571, 1559, 1523, 1507, 1457, 1379, 1246, 1096, 1065, 1027, 891 cm$^{-1}$. LRMS (EI): Mass calcd for C$_{19}$H$_{22}$ClFeN [M]+, 355.1, 356.1, 357.1. Found 355.2, 356.2, 357.2.

Example 2

Pentamethyl-η$^5$-cyclopentadienyl (ethyl 1-methyl-η$^5$-cyclopenta[b]pyridinyl-3-carboxylate)iron (Racemic Synthesis) (±-2a)

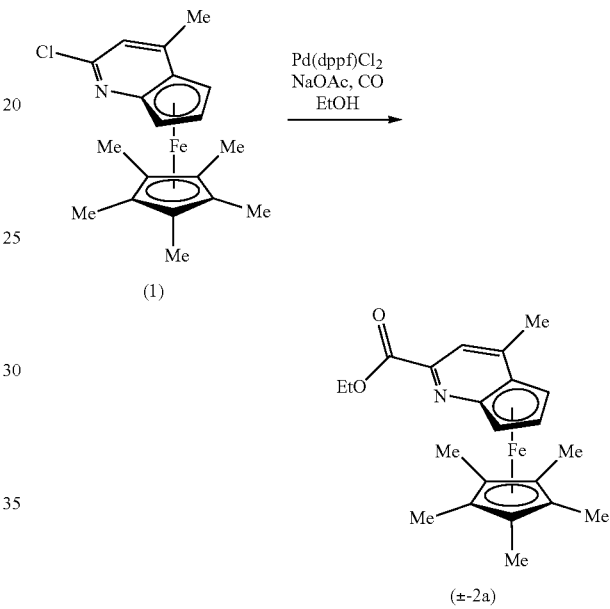

(±-2a)

To a solution of iron(II) 1,2,3,4,5-pentamethylcyclopenta-2,4-dien-1-ide 2-chloro-4-methyl-5H-cyclopenta[b]pyridin-5-ide (1) (1.0 g, 2.8 mmol) in ethanol (60 mL) is added dry sodium acetate (0.46 g, 5.6 mmol). The solution is then degassed by sparging with nitrogen for 30 minutes, after which Pd(dppf)Cl$_2$ (165 mg, 0.23 mmol) is then added. Carbon monoxide is then bubbled through the solution for 15 minutes and then the solution is kept under an atmosphere of carbon monoxide (balloon). The reaction is heated at 75° C. and stirred for 6~12 hours (monitoring by TLC analysis, 20% EtOAc/Hex). After the reaction is deemed complete by TLC analysis, the reaction is filtered through celite, washed with DCM, and then concentrated. The residue is then partitioned between ethyl acetate and water, separated, and the organic layer is washed with brine, dried over MgSO$_4$, filtered, and concentrated. The crude material is then purified by flash chromatography on silica gel (20% EtOAc/Hex) to provide the pure ester as a blue/green solid (1.04 g, 2.64 mmol, 94% yield). Note: The ester decomposes when standing in air at ambient temperature, stable >2 months at −30° C. Analytical data for (3): $^1$H NMR (500 MHz, CDCl$_3$) δ 7.47 (q, J=1.04 Hz, 1H), 5.00 (dd, J=1.09 Hz, 1H), 4.51 (m, 2H), 4.44 (dq, J=1.63 Hz, 1H), 4.07 (t, J=2.75 Hz, 1H), 2.46 (d, J=1.13 Hz, 3H), 1.61 (s, 15H), 1.43 (t, J=7.09 Hz, 3H); $^{13}$C NMR (126 MHz, CDCl$_3$) δ 165.97, 151.56, 149.26, 115.43, 108.03, 84.55, 79.08, 78.78, 68.55, 62.77, 61.70, 19.78, 14.64, 10.01. IR (neat) ν 2970, 2904, 1736, 1710, 1531, 1468, 1372, 1349, 1322, 1220, 1182, 1106, 1029 cm$^{-1}$. LRMS (EI): Mass calcd for C14H13Br [M]+, 260.0, 262.0. Found 260.1, 262.1.

Example 3

Pentamethyl-η$^5$-cyclopentadienyl (1-methyl-η$^5$-cyclopenta[b]pyridinyl-3-carbaldehyde)iron (Racemic Aldehyde)

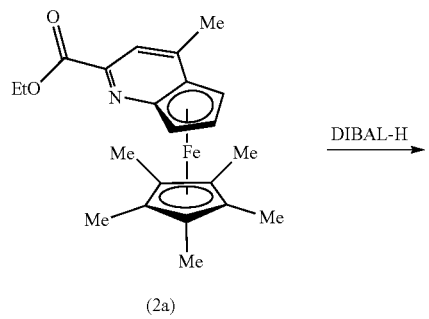

Diisobutylaluminum hydride (1M in hexane, 2 equiv) is added dropwise to a solution of ferrocenyl ester (2a) (1 equiv, 1.0 g) in toluene (0.7 M) at −78° C. and stirred for 2 hours at the same temperature. The reaction is carefully quenched with MeOH (3 equiv) at −78° C. A saturated solution of potassium sodium tartrate is added to the reaction mixture and warmed to ambient temperature and stirred for 2 hours. The reaction mixture is then transferred to a separatory funnel and diluted with ethyl acetate. The organic layer is separated and the aqueous layer was extracted with EtOAc (2×20 mL), the combined organics are then dried over Na$_2$SO$_4$ and concentrated in vacuo. The crude product is purified by flash chromatography on silica gel (5% EtOAc/Hex) to afford the corresponding ferrocenyl aldehyde as a green solid (0.59 g, 56%) (3). Note: The aldehyde is bench stable (>2 months). Analytical data for the aldehyde: $^1$H NMR (500 MHz, CDCl$_3$) δ 9.97 (s, 1H), 7.33 (d, J=1.24 Hz, 1H), 4.92 (dd, J=1.03, 2.85 Hz, 1H), 4.54 (dd, J=1.09, 2.88 Hz, 1H), 4.20 (t, J=2.77 Hz, 1H), 2.47 (d, J=1.16 Hz, 3H), 1.59 (s, 15H); $^{13}$C NMR (126 MHz, CDCl$_3$) δ 193.56, 155.00, 151.67, 111.70, 107.90, 85.39, 79.98, 78.98, 68.57, 63.87, 19.84, 9.91. IR (neat) ν 2923, 2854, 1693, 1539, 1457, 1375, 1309, 1147, 1027, 851, 773, 700 cm$^{-1}$. LRMS (EI): Mass calcd for C$_{20}$H$_{24}$FeNO [M+H]$^+$, 250.1. Found 250.2.

Example 4

Pentamethyl-η$^5$-cyclopentadienyl (N-((1S,2S)-1-hydroxy-1-phenylpropan-2-yl)-N,1-dimethyl-η$^5$-cyclopenta[b]pyridinyl-3-carboxamide)iron A flame dried 2 dram vial equipped with a stirbar is charged with Pentamethyl-η$^5$-cyclopentadienyl (3-chloro-1-methyl-η$^5$-cyclopenta[b]pyridinyl)iron (1) (100 mg, 0.281 mmol), sodium acetate (46.1 mg, 0.562 mmol), and (1S,2S)-(+)-pseudoephedrine (93.0 mg, 0.562 mmol). The vial is then taken into the glovebox where Pd(dppf)Cl$_2$ (16.5 mg, 0.022 mmol) is added and the vial is then sealed with a screw cap with teflon coated septa. After taking the vial out of the glovebox, toluene (1.5 mL) is added and then carbon monoxide is bubbled through the solution for 15 minutes. The reaction mixture is then heated to 70° C. under carbon monoxide (1 atm, balloon). After the reaction is deemed complete by TLC analysis (50% EtOAc/Hexanes, 6 hours, Rf~0.25 (dark blue, no stain), Rf~0.15 (lavender, no stain)) the reaction mixture is allowed to cool to ambient temperature, opened to air, and stirred for 15 minutes. The crude reaction mixture is then directly loaded onto a column of silica gel (30-80% EtOAc/Hexanes) to afford the pure diastereomers (88 mg, 61% combined yield) as dark purple solids. Absolute configurations are determined from the crystal structure of the NHC prepared from the corresponding material. Note: The amide decomposes at ambient temperature in air, but can be stored at −30° C.>2 months. Analytical data for the (+)-amide Rf~0.25: $^1$H NMR (500 MHz, $C_6D_6$) δ 8.10 (d, J=7.5 Hz, 1H), 7.38 (d, J=7.5 Hz, 2H), 7.32 (s, 1H), 7.07 (d, J=7.4 Hz, 1H), 4.89 (d, J=2.7 Hz, 1H), 4.59 (m, 2H), 4.07 (d, J=2.8 Hz, 1H), 3.78 (m, 1H), 3.10 (s, 3H), 2.06 (s, 3H), 1.51 (s, 15H), 0.58 (d, J=5.4 Hz, 3H); $^{13}$C NMR (126 MHz, $CD_2Cl_2$) δ 168.86, 155.14, 153.91, 144.23, 128.34, 127.41, 127.03, 116.90, 105.89, 83.38, 79.06, 78.17, 75.59, 66.61, 62.42, 58.56, 26.80, 19.55, 16.19, 9.78. IR (neat) ν 3233, 2905, 2361, 1698, 1635, 1559, 1473, 1456, 1381, 1285, 1054, 1027, 768, 729, 702 cm$^{-1}$. LRMS (EI): Mass calcd for $C_{30}H_{37}FeN_2O_2$ [M+H]$^+$, 513.2. Found 513.3.

Example 5

(+)-Pentamethyl-η$^5$-cyclopentadienyl (1-methyl-η$^5$-cyclopenta[b]pyridinyl-3-carbaldehyde)iron (3)

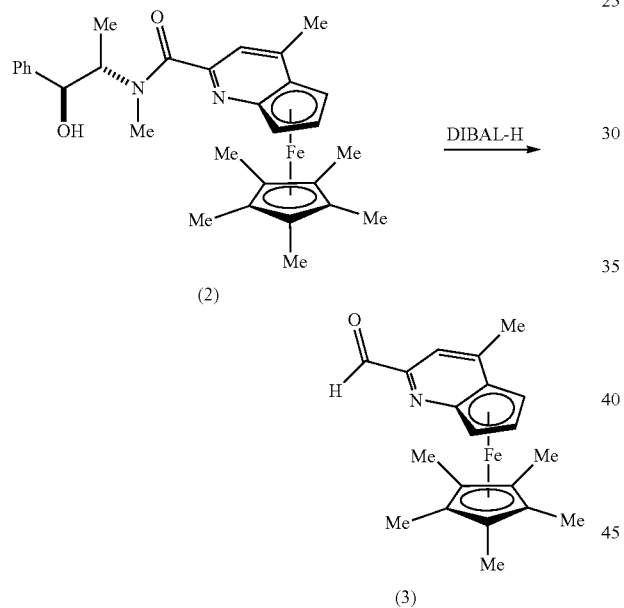

Diisobutylaluminum hydride (0.9 M in hexane, 0.43 mL, 0.39 mmol) is added dropwise to a solution of pseudoephedrine amide (2) (50 mg, 0.10 mmol) in THF (2 mL) at −78° C. (acetone/CO$_2$(s)) and the reaction mixture is allowed to stir at −78° C. for 2 hours (the reaction is monitored by TLC analysis (50% EtOAc/Hex, reaction quenched with methanol in spotter)). Once the reaction is deemed complete, it is carefully quenched with wet MeOH at −78° C. The reaction mixture is then diluted with diethyl ether and a saturated solution of potassium sodium tartrate is added. The reaction mixture is then warmed to ambient temperature and stirred for 4 hours. The organic layer is then separated and the aqueous layer is extracted with diethyl ether (3×10 mL) The combined organic layers are then washed with brine, dried over MgSO$_4$, and concentrated in vacuo. The crude product is purified by flash chromatography on silica gel (10-20% EtOAc/Hex, green band) to afford the corresponding ferrocenyl aldehyde as a green solid (27 mg, 78% yield) (3). Note: The aldehyde is bench stable (>2 months). Analytical data for the aldehyde matches that of the racemic: $^1$H NMR (500 MHz, CDCl$_3$) δ 9.97 (s, 1H), 7.33 (d, J=1.24 Hz 1H), 4.92 (dd, J=1.03, 2.85 Hz, 1H), 4.54 (dd, J=1.09, 2.88 Hz, 1H), 4.20 (t, J=2.77 Hz, 1H), 2.47 (d, J=1.16 Hz, 3H), 1.59 (s, 15H); $^{13}$C NMR (126 MHz, CDCl$_3$) δ 193.56, 155.00, 151.67, 111.70, 107.90, 85.39, 79.98, 78.98, 68.57, 63.87, 19.84, 9.91. IR (neat) ν 2923, 2854, 1693, 1539, 1457, 1375, 1309, 1147, 1027, 851, 773, 700 cm$^{-1}$. LRMS (EI): Mass calcd for $C_{20}H_{24}FeNO$ [M+H]$^+$, 250.1. Found 250.2. Enantiomeric ratio was measured by chiral phase HPLC (Regis (S,S)-Whelk-01, 25 cm×4.6 mm; 5% IPA/hexanes 0.7 mL/min, 254 nm), Rt1 (−)=25.1 min, Rt2 (+)=27.5 min; >99% ee. Rt2 (+) [α]$_D^{20}$=+22.4° (c=0.005, MeOH).

Example 6

(+)-Ferrocenyl Mesityl Imidazolium Chloride (4a')

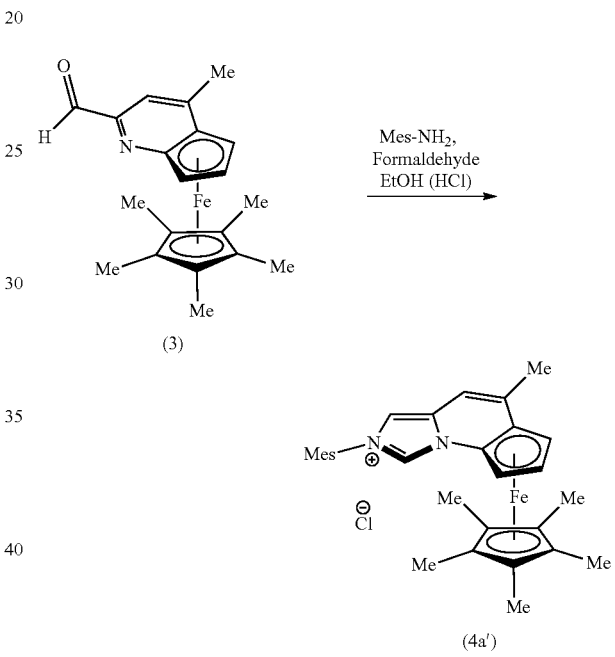

The NHCs disclosed herein are prepared by of modified literature procedure (Hutt, J. T. et al., Org. Lett. 2011, 13, 5256, incorporated herein by reference). A 2 dram vial equipped with a stir bar is charged with formaldehyde (37%, 181 mg, 2.23 mmol), THF (5 mL), and 2,4,6-trimethylaniline (166 mg, 1.23 mmol). The mixture is stirred at ambient temperature for 20 minutes and then HCl (3.0 M in EtOH, 0.457 mL, 1.34 mmol) is added and the mixture is stirred for 30 minutes. Pentamethyl-η$^5$-cyclopentadienyl (1-methyl-η$^5$-cyclopenta[b]pyridinyl-3-carbaldehyde)iron (3) (390 mg, 1.1 mmol) is then added, and the reaction is allowed to stir at ambient temperature for 3 hours and then concentrated. The crude residue is purified by flash chromatography on neutral alumina (acetone to 5:1, acetone:EtOH), and then the residue is washed with 5:1 Et$_2$O:EtOAc to afford the NHC as an orange solid (398 mg, 69%). Note: On occasion the reaction does not go to completion, in these cases the starting material. is isolated and resubjected to the reaction conditions. Note: The NHCs are bench stable, but hydroscopic and should be stored in a desiccator or glovebox. Analytical data for (4a'): $^1$H NMR (500 MHz, CDCl$_3$) δ 12.28 (s, 1H), 7.18 (s, 1H), 7.03 (d, J=14.7 Hz, 2H), 7.00 (s, 1H), 6.82 (s, 1H), 6.29 (s, 1H), 4.16 (d, J=2.60 Hz, 1H), 3.99 (m, 1H), 2.37 (s, 3H), 2.34 (s, 3H), 2.23 (s, 3H), 2.08 (s, 3H), 1.62 (s, 15H); $^{13}$C NMR (126 MHz, CDCl$_3$) δ 141.18, 141.09, 134.68, 133.78, 131.57, 130.59, 130.14, 130.05, 113.89, 105.16, 90.14, 81.46, 77.36, 76.98, 76.61, 73.63, 65.76, 64.94, 21.24, 19.51, 18.15, 17.96, 10.01. IR (neat) ν 3296, 3061, 2969, 2910, 1699, 1629, 1568, 1498, 1479, 1379, 1259, 1218, 1031 cm$^{-1}$.

Example 7

(+)-Ferrocenyl Mesityl Imidazolium Tetrafluoroborate (4a)

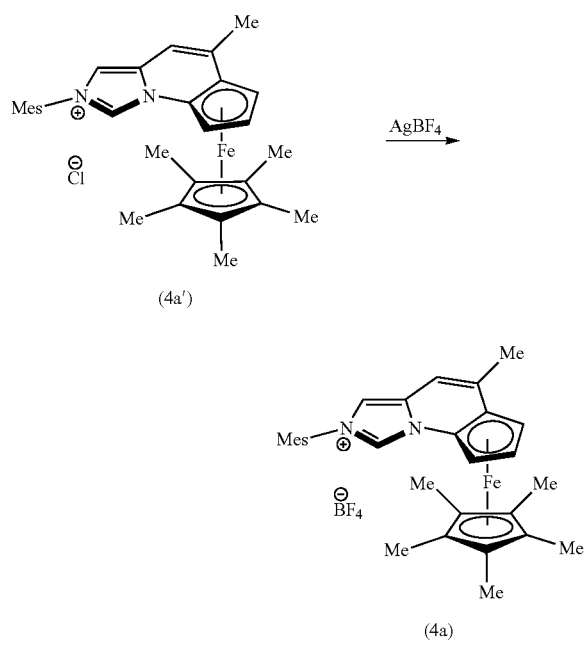

A flame-dried 2 dram vial equipped with a stirbar is charged with the ferrocenyl imidazolium chloride (150 mg, 0.29 mmol) (4a'). The solid is then dissolved in acetonitrile (2.9 mL) and then silver tetrafluoroborate (68 mg, 0.35 mmol) is added. The reaction mixture is allowed to stir at ambient temperature under nitrogen for 16 hours. The reaction mixture is then concentrated in vacuo and the crude residue is purified by flash chromatography on neutral alumina (Acetone:EtOH, 7:1) to afford the pure tetrafluoroborate salt of the NHC (4a) as an orange/red solid (149 mg, 90% yield). Analytical data for 5: $^1$H NMR (500 MHz, CDCl$_3$) δ 10.10 (s, 1H), 7.24 (d, J=1.48 Hz 1H), 7.05 (s, 1H), 7.02 (s, 1H), 6.86 (s, 1H), 5.60 (m, 1H), 4.20 (m, 1H), 4.04 (q, J=2.55 Hz, 1H), 2.39 (s, 3H), 2.36 (s, 3H), 2.18 (s, 3H), 2.01 (s, 3H), 1.66 (s, 15H); $^{13}$C NMR (126 MHz, CDCl$_3$) δ 141.46, 141.37, 134.68, 133.77, 131.33, 131.06, 130.14, 130.03, 129.92, 114.57, 105.25, 89.81, 81.56, 73.86, 66.04, 63.31, 21.31, 19.54, 17.78, 17.51, 9.84. IR (neat) ν 3118, 2909, 1628, 1569, 1457, 1383, 1062 cm$^{-1}$. [α]$_D^{20}$=+38.5° (c=0.01, MeOH).

Example 8

(+)-Ferrocenyl Phenyl Imidazolium Chloride (4b')

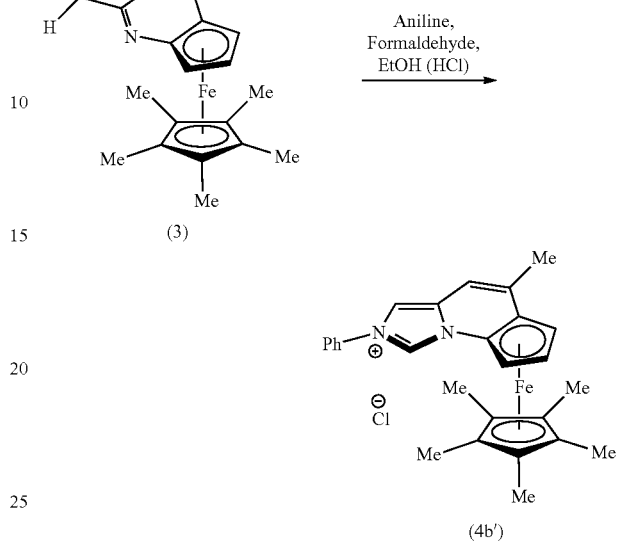

A 2 dram vial equipped with a stir bar is charged with formaldehyde (37%, 23.2 mg, 0.286 mmol), THF (1.5 mL), and aniline (16.0 mg, 0.17 mmol). The mixture is stirred at ambient temperature for 30 minutes and then HCl (3.0 M in EtOH, 0.110 mL, 0.329 mmol) is added and the mixture is stirred for 30 minutes. (+)-Pentamethyl-η$^5$-cyclopentadienyl (1-methyl-η$^5$-cyclopenta[b]pyridinyl-3-carbaldehyde)iron (3) (50 mg, 0.143 mmol) is then added, and the reaction is allowed to stir at ambient temperature for 3 hours while monitoring by TLC analysis (90:10:1, DCM:MeOH:AcOH, Rf~0.25). The crude residue is purified by flash chromatography on neutral alumina (acetone to 5:1, acetone:EtOH), and then the residue is washed with 5:1 Et$_2$O:EtOAc to afford the NHC as an orange solid (47.2 mg, 70%) (4b'). Analytical data: $^1$H NMR (500 MHz, CDCl$_3$) δ 12.76 (s, 1H), 8.08 (s, 2H), 7.74 (s, 1H), 7.60 (s, 2H), 7.47 (s, 1H), 6.82 (s, 1H), 6.21 (s, 1H), 4.15 (s, 1H), 3.99 (s, 1H), 2.34 (s, 3H), 1.63 (s, 17H); $^{13}$C NMR (126 MHz, CDCl$_3$) δ 141.46, 134.98, 131.09, 130.90, 130.00, 121.56, 110.65, 105.22, 89.42, 81.58, 73.75, 65.98, 65.03, 19.56, 9.84. IR (neat) ν 3060, 2908, 1629, 1598, 1570, 1467, 1381, 1276, 1073, 1031, 829, 802 cm$^{-1}$. LRMS (EI): Mass calcd for $C_{27}H_{29}FeN_2$ [M]$^+$, 437.2. Found 437.3.

Example 9

(+)-Ferrocenyl Phenyl Imidazolium Tetrafluoroborate (4b)

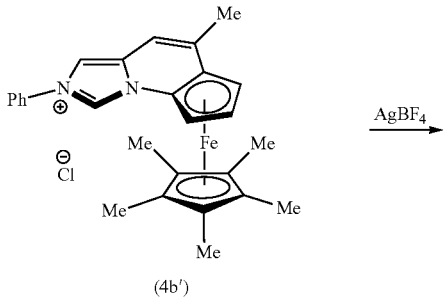

-continued

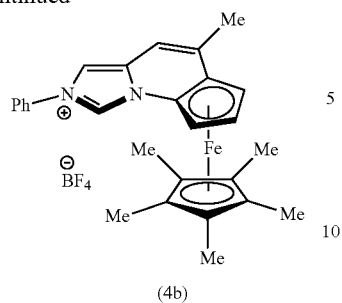

(4b)

-continued

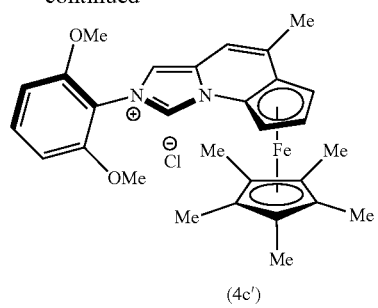

(4c')

A flame-dried 2 dram vial equipped with a stirbar is charged with the ferrocenyl imidazolium chloride (35 mg, 0.074 mmol) (4b'). The solid is then dissolved in acetonitrile (1 mL) and then silver tetrafluoroborate (17.3 mg, 0.089 mmol) is added. The reaction mixture is allowed to stir at ambient temperature under nitrogen for 16 hours. The reaction mixture is then concentrated in vacuo and the crude residue is purified by flash chromatography on neutral alumina (acetone:EtOH, 7:1) to afford the pure tetrafluoroborate salt of the NHC as an orange/red solid (4b) (34 mg, 88% yield). Analytical data: $^1$H NMR (500 MHz, CDCl$_3$) δ 10.78 (s, 1H), 7.86, 7.80 (m, 2H), 7.78 (d, J=3.8 Hz, 1H), 7.48 (m, 2H), 7.40 (t, J=7.5 Hz, 1H), 6.84 (d, J=1.6 Hz, 1H), 5.61 (s, 1H), 4.19 (s, 1H), 4.10 (m, 1H), 3.99 (d, J=2.7 Hz, 1H), 2.31 (s, 3H), 1.58 (d, J=1.4 Hz, 16H).; $^{13}$C NMR (126 MHz, CDCl$_3$) δ 141.25, 134.65, 131.33, 130.82, 130.19, 126.86, 121.53, 111.68, 105.44, 88.93, 81.58, 77.36, 73.74, 66.11, 63.43, 19.48, 9.61. IR (neat) ν 3060, 2908, 2854, 2360, 1630, 1383, 1072, 690, 589 cm$^{-1}$. LRMS (EI): Mass calcd for $C_{27}H_{29}FeN_2$ [M]$^+$, 437.2. Found 437.3. $[\alpha]_D^{20}$=+53.5° (c=0.01, MeOH).

Example 10

(+)-Ferrocenyl 2,6-dimethoxyphenyl imidazolium chloride (4c')

A 2 dram vial equipped with a stir bar is charged with formaldehyde (37%, 69.7 mg, 0.859 mmol), THF (4.5 mL), and 2,6-dimethoxyaniline (79.0 mg, 0.515 mmol). The mixture is stirred at ambient temperature for 30 minutes and then HCl (3.0 M in EtOH, 0.329 mL, 0.988 mmol) is added and the mixture is stirred for 30 minutes. (+)-Pentamethyl-η$^5$-cyclopentadienyl (1-methyl-η$^5$-cyclopenta[b]pyridinyl-3-carbaldehyde)iron (3) (150 mg, 0.429 mmol) is then added, and the reaction is allowed to stir at ambient temperature for ~3 hours while monitoring by TLC analysis (90:10:1, DCM:MeOH:AcOH, Rf~0.25). The crude residue is purified by flash chromatography on neutral alumina (acetone to 5:1, acetone:EtOH), and then the residue is washed with 5:1 Et$_2$O:EtOAc to afford the NHC as an orange solid (4c') (148 mg, 65%). Analytical data: $^1$H NMR (500 MHz, Methanol-d$_4$) δ 11.85 (s, 1H), 7.42 (t, J=8.3 Hz, 1H), 7.28 (s, 1H), 6.80 (s, 1H), 6.72 (d, J=8.4 Hz, 2H), 6.32 (s, 1H), 4.11 (d, J=2.3 Hz, 1H), 3.96 (d, J=2.5 Hz, 1H), 3.89 (s, 6H), 2.34 (s, 3H), 1.68 (s, 19H). $^{13}$C NMR (126 MHz, CDCl$_3$) δ 154.98, 139.56, 134.01, 132.11, 129.40, 115.50, 113.29, 105.53, 104.93, 89.72, 81.45, 76.65, 73.29, 65.61, 65.03, 56.84, 19.45, 9.83. IR (neat) ν 3022, 2898, 2362, 1624, 1603, 1541, 1258, 1115, 1029, 779 cm$^{-1}$. LRMS (EI): Mass calcd for $C_{29}H_{33}FeN_2O_2$ [M]$^+$, 497.2. Found 497.3.

Example 11

(+)-Ferrocenyl 2,6-dimethoxyphenyl imidazolium tetrafluoroborate (4c)

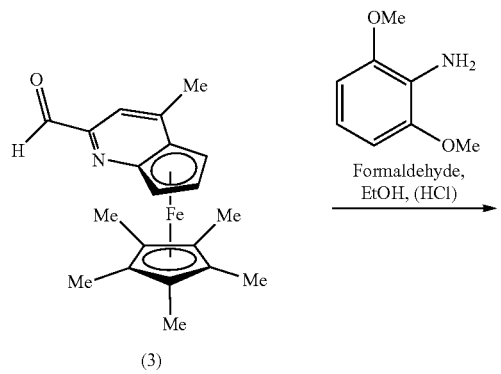

(3)

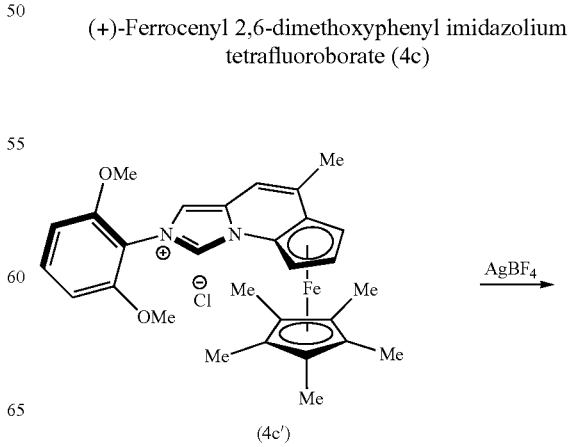

(4c')

-continued

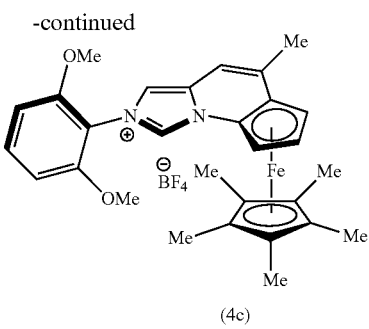

(4c)

A flame-dried 2 dram vial equipped with a stirbar is charged with the ferrocenyl imidazolium chloride (35 mg, 0.066 mmol) (4c') The solid is then dissolved in acetonitrile (1 mL) and then silver tetrafluoroborate (15.3 mg, 0.079 mmol) is added. The reaction mixture is allowed to stir at ambient temperature under nitrogen for 16 hours. The reaction mixture is then concentrated in vacuo and the crude residue is purified by flash chromatography on neutral alumina (acetone:EtOH, 7:1) to afford the pure tetrafluoroborate salt of the NHC as an orange/red solid (4c) (33 mg, 86% yield). Analytical data: $^1$H NMR (500 MHz, Methanol-d$_4$) δ 8.61 (s, 2H), 8.56 (s, 1H), 8.33 (s, 1H), 7.11 (s, 1H), 4.99 (d, J=2.5 Hz, 1H), 4.51 (d, J=2.6 Hz, 1H), 4.21 (t, J=2.6 Hz, 1H), 2.44 (s, 3H), 1.64 (s, 15H); $^{13}$C NMR (126 MHz, CDCl$_3$) δ 142.59, 138.13, 135.16, 134.89, 133.08, 125.16, 124.93, 124.34, 122.99, 115.02, 107.10, 89.93, 82.75, 78.85, 74.74, 67.99, 63.05, 49.85, 49.46, 49.28, 29.53, 19.48, 9.67. IR (neat) ν 3128, 3060, 2946, 2909, 1632, 1603, 1486, 1266, 1114, 1031, 729 cm$^{-1}$. LRMS (EI): Mass calcd for C$_{29}$H$_{33}$FeN$_2$O$_2$ [M]$^+$, 497.2. Found 497.3. [α]$_D^{20}$=+47.8° (c=0.01, MeOH).

Example 12

(+)-Ferrocenyl 3,5-bis(trifluoromethyl)phenyl imidazolium chloride (4d')

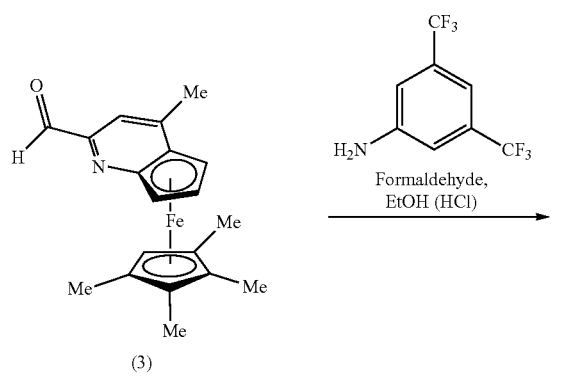

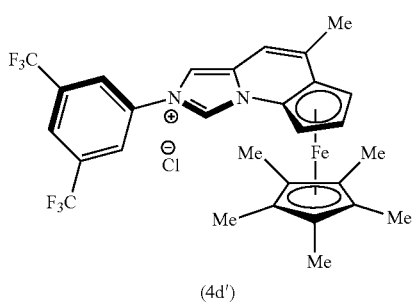

(4d')

A 2 dram vial equipped with a stir bar is charged with formaldehyde (37%, 69.7 mg, 0.859 mmol), THF (4.5 mL), and 3,5-bis(trifluoromethyl)aniline (118.0 mg, 0.515 mmol). The mixture is stirred at ambient temperature for 1 hour and then HCl (3.0 M in EtOH, 0.329 mL, 0.988 mmol) is added and the mixture is stirred for 30 minutes. (+)-Pentamethyl-η$^5$-cyclopentadienyl (1-methyl-η$^5$-cyclopenta[b]pyridinyl-3-carbaldehyde)iron (3) (150 mg, 0.429 mmol) is then added, and the reaction is allowed to stir at ambient temperature for 24 hours while monitoring by TLC analysis (90:10:1, DCM:MeOH:AcOH, Rf~0.25). After 24 hours the reaction mixture is diluted with diethyl ether:pentane (1:1) and the resulting precipitate is filtered and washed with additional portions of ether:pentane to provide the NHC as a bright orange solid (133 mg, 51%) (4d'). Analytical data: $^1$H NMR (500 MHz, CDCl$_3$) δ 10.58 (s, 1H), 8.60 (s, 2H), 8.55 (s, 1H), 8.33 (s, 1H), 7.10 (s, 1H), 4.98 (d, J=2.6 Hz, 1H), 4.51 (s, 1H), 4.27-4.16 (m, 1H), 2.43 (s, 3H), 1.67-1.61 (m, 15H); $^{13}$C NMR (126 MHz, CDCl$_3$) δ 142.59, 135.15, 134.87, 133.07, 124.32, 114.99, 107.07, 89.92, 82.74, 78.84, 74.72, 67.98, 63.01, 49.45, 19.46, 9.65. IR (neat) ν 3028, 2910, 2799, 1622, 1406, 1281, 1138, 1081, 1034, 698 cm$^{-1}$. LRMS (EI): Mass calcd for C$_{29}$H$_{27}$F$_6$FeN$_2$ [M]$^+$, 573.1. Found 573.3.

Example 13

(+)-Ferrocenyl phenyl 3,5-bis(trifluoromethyl)phenyl tetrafluoroborate (4d)

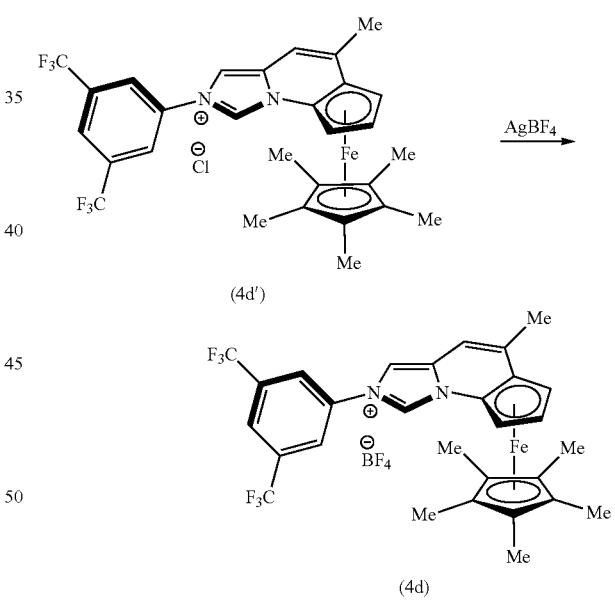

A flame-dried 2 dram vial equipped with a stirbar is charged with the ferrocenyl imidazolium chloride (25 mg, 0.041 mmol) (4d'). The solid is then dissolved in acetonitrile (1 mL) and then silver tetrafluoroborate (9.6 mg, 0.049 mmol) is added. The reaction mixture is allowed to stir at ambient temperature under nitrogen for 16 hours. The reaction mixture is then concentrated in vacuo and the crude residue is purified by flash chromatography on neutral alumina (acetone:EtOH, 7:1) to afford the pure tetrafluoroborate salt of the NHC as an dark red solid (4d) (20.0 mg, 74% yield). Analytical data: $^1$H NMR (500 MHz, CDCl$_3$) δ 10.10 (s, 1H), 7.24 (d, J=1.48 Hz 1H), 7.05 (s, 1H), 7.02 (s, 1H), 6.86 (s, 1H), 5.60 (m, 1H), 4.20 (m, 1H), 4.04 (q, J=2.55 Hz, 1H), 2.39 (s, 3H), 2.36 (s, 3H), 2.18 (s, 3H), 2.01 (s, 3H), 1.66 (s, 15H); $^{13}$C NMR (126 MHz, CDCl$_3$) δ 141.46, 141.37, 134.68, 133.77, 131.33, 131.06, 130.14, 130.03, 129.92, 114.57, 105.25, 89.81, 81.56, 73.86, 66.04, 63.31, 21.31, 19.54, 17.78, 17.51, 9.84. IR (neat) ν 2917, 1708, 1622, 1572, 1474, 1384, 1280, 1180, 1081, 1035, 900, 534 cm$^{-1}$. LRMS (EI): Mass calcd for C$_{29}$H$_{27}$F$_6$FeN$_2$ [M]$^+$, 573.1. Found 573.3. [α]$_D^+$=+20.6° (c=0.01, MeOH).

Example 14

(−)-Ferrocenyl mesityl imidazolium Copper Chloride Complex (−)-4a-CuCl

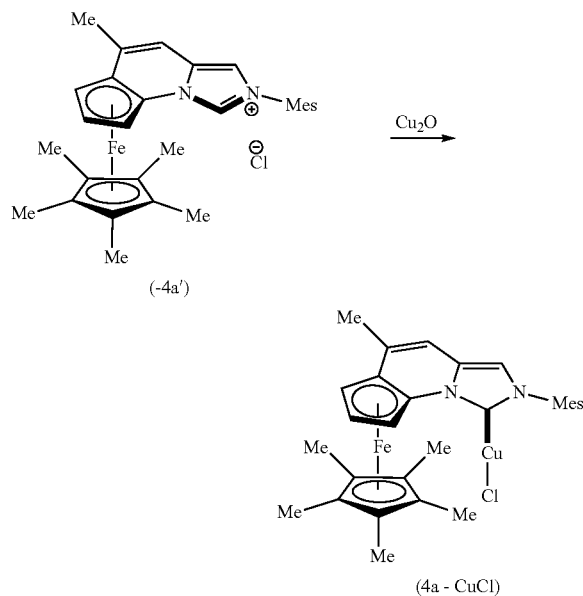

A flame-dried 2 dram vial equipped with a stirbar is brought into the glovebox and charged with the (−)ferrocenyl imidazolium chloride (20 mg, 0.039 mmol) and copper(I) oxide (5.3 mg, 0.037 mmol). The vial is then sealed with a screw-cap with a teflon coated septa and then brought out of the glovebox. THF (0.37 mL) is then added and the mixture is heated to 60° C. After 24 hours the solution is concentrated and the crude residue is purified by column chromatography on silica gel (DCM, Rf~0.4) to provide the complex as an orange solid (18 mg, 0.031 mmol). X-ray quality crystals are obtained by vapor diffusion (DCM/pentane, −30° C.). Analytical data: $^1$H NMR (500 MHz, CDCl$_3$) δ 7.08 (s, 1H), 7.07 (s, 1H), 7.05 (s, 1H), 6.78 (s, 1H), 5.43 (m, 1H), 4.09 (s, 1H) 3.89 (d, J=2.89 Hz, 1H), 2.39 (s, 3H), 2.29 (s, 3H), 2.29 (s, 3H), 2.16 (s, 3H), 1.97 (s, 3H), 1.67 (s, 15H); $^{13}$C NMR (126 MHz, CDCl$_3$) δ 139.85, 136.62, 136.55, 135.53, 134.80, 131.51, 129.70, 129.66, 114.72, 107.96, 93.73, 81.21, 77.37, 71.73, 65.53, 62.79, 30.10, 21.27, 19.28, 18.35, 17.96, 10.22.

NHC-Catalyzed Annulation

Example 15

Ethyl 5-oxo-2,3-diphenyltetrahydrofuran-2-carboxylate General Procedure

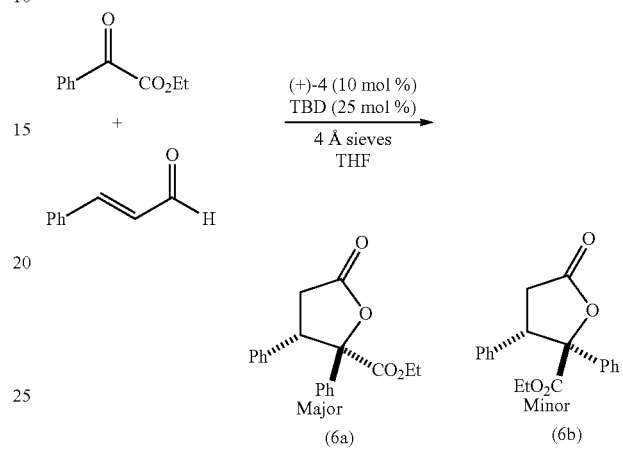

A flame dried 2 dram vial equipped with a stirbar is brought into the glovebox and charged with (+)-4 (0.016 mmol, 0.10 equiv), TBD (6.6 mg, 0.048 mmol, 0.30 equiv), and 4 Å molecular sieves (100 mg). The vial is then sealed with a screw cap equipped with a teflon septa. The vial is then taken out of the glovebox and THF (0.80 mL), ethyl 2-oxo-2-phenylacetate (57 mg, 0.32 mmol, 2.0 equiv) and cinnamaldehyde (21 mg, 0.16 mmol) are added. The reaction mixture is then stirred at 23° C. for 36 hours (monitored by GC/MS). The crude reaction mixture is filtered through celite and an aliquot is taken to determine dr. After filtration the crude mixture is concentrated and the crude residue is purified by column chromatography on silca gel (2% EtOAc/Hex) to provide the pure products. Analytical data matches that reported in the literature (Li, Y. et al., *Adv. Synth. Catal.* 2008, 350, 1885, incorporated herein by reference). Major diastereomer (Cis) $^1$H NMR (500 MHz, CDCl$_3$): δ 7.72-7.67 (m, 2H), 7.45-7.27 (m, 8H), 4.08 (dd, J=8.4, 4.1 Hz, 1H), 3.87-3.80 (m, 2H), 2.88 (dd, J=17.6, 8.4 Hz, 1H), 2.79 (dd, J=17.7, 4.1 Hz, 1H), 0.89 (d, J=7.7 Hz, 3H). Enantiomeric ratio is determined by chiral phase HPLC (chiralcel AD-H; i-PrOH-hexane, 2:98, 1.0 mL/min, 210 nm); t$_r$ (major)=39.4 min, t$_r$ (major)=60.0 min. and t$_r$ (minor)=17.1 min, t$_r$ (minor)=18.7 min. Absolute stereochemistry is assigned by analogy.

Example 16

Ethyl 5-oxo-2,3-diphenyltetrahydrofuran-2-carboxylate (6)

A flame dried 2 dram vial equipped with a stirbar is brought into the glovebox and charged with (+)-4a (9.0 mg, 0.016 mmol, 0.10 equiv), TBD (6.6 mg, 0.048 mmol, 0.30 equiv), and 4 Å molecular sieves (100 mg). The vial is then sealed with a screw cap equipped with a teflon septa. The vial is then taken out of the glovebox and THF (0.80 mL), ethyl 2-oxo-2-phenylacetate (57 mg, 0.32 mmol, 2.0 equiv) and cinnamaldehyde (21 mg, 0.16 mmol) are added. The reaction mixture is then stirred at 23° C. for 36 hours (monitored by GC/MS).

The crude reaction mixture is filtered through celite and an aliquot is taken to determine dr. After filtration the crude mixture is concentrated and the crude residue is purified by column chromatography on silca gel (2% EtOAc/Hex) to provide the pure products (6a) and (6b). Analytical data matches that reported in the literature. Major diastereomer (Cis) $^1$H NMR (500 MHz, CDCl$_3$): δ 7.72-7.67 (m, 2H), 7.45-7.27 (m, 8H), 4.08 (dd, J=8.4, 4.1 Hz, 1H), 3.87-3.80 (m, 2H), 2.88 (dd, J=17.6, 8.4 Hz, 1H), 2.79 (dd, J=17.7, 4.1 Hz, 1H), 0.89 (d, J=7.7 Hz, 3H). Enantiomeric ratio is determined by chiral phase HPLC (chiralcel AD-H; i-PrOH-hexane, 2:98, 1.0 mL/min, 210 nm); t$_r$ (major)=39.4 min, t$_r$ (major)=60.0 min. and t$_r$ (minor)=17.1 min, t$_r$ (minor)=18.7 min.

Example 17

Ethyl 5-oxo-2,3-diphenyltetrahydrofuran-2-carboxylate (6)

A flame dried 2 dram vial equipped with a stirbar is brought into the glovebox and charged with (+)-4c (9.3 mg, 0.016 mmol, 0.10 equiv), TBD (6.6 mg, 0.048 mmol, 0.30 equiv), and 4 Å molecular sieves (100 mg). The vial is then sealed with a screw cap equipped with a teflon septa. The vial is then taken out of the glovebox and THF (0.80 mL), ethyl 2-oxo-2-phenylacetate (57 mg, 0.32 mmol, 2.0 equiv) and cinnamaldehyde (21 mg, 0.16 mmol) are added. The reaction mixture is then stirred at 23° C. for 36 hours (monitored by GC/MS). The crude reaction mixture is filtered through celite and an aliquot is taken to determine dr. After filtration the crude mixture is concentrated and the crude residue is purified by column chromatography on silca gel (2% EtOAc/Hex) to provide the pure products (30.2 mg, 0.097 mmol, 61.2% yield) (6a) and (6b). Analytical data matches that reported in the literature. Major diastereomer (Cis) $^1$H NMR (500 MHz, CDCl$_3$): δ 7.72-7.67 (m, 2H), 7.45-7.27 (m, 8H), 4.08 (dd, J=8.4, 4.1 Hz, 1H), 3.87-3.80 (m, 2H), 2.88 (dd, J=17.6, 8.4 Hz, 1H), 2.79 (dd, J=17.7, 4.1 Hz, 1H), 0.89 (d, J=7.7 Hz, 3H). Enantiomeric ratio is determined by chiral phase HPLC (chiralcel AD-H; i-PrOH-hexane, 2:98, 1.0 mL/min, 210 nm); t$_r$ (major)=39.4 min, t$_r$ (major)=60.0 min. and t$_r$ (minor)=17.1 min, t$_r$ (minor)=18.7 min.

Transition Metal Catalyzed Transformations

Example 18

NHC/Cu-catalyzed Conjugate Borylation

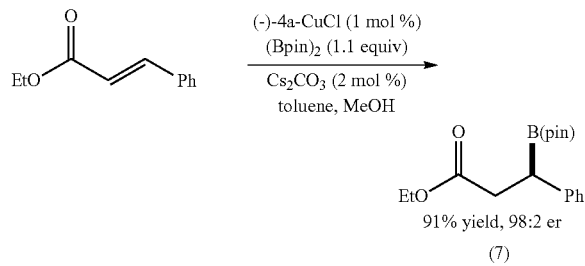

A flame-dried 2 dram vial equipped with a teflon coated stir bar is brought into the glovebox and charged with (S)-4a-CuCl (1.16 mg, 0.002 mmol), bis(pinacolato)diboron (55.9 mg, 0.22 mmol), and cesium carbonate (1.30 mg, 0.004 mmol). The vial is then sealed with a teflon coated septa equipped screw cap and taken out of the glovebox. Toluene (1 mL) is then added and the solution is allowed to stir for 10 minutes before being cooled to 0° C. Trans-ethyl cinnamate (35.2 mg, 0.20 mmol) and methanol (12.8 mg, 0.40 mmol) are then simultaneously added to the reaction mixture at 0° C. The reaction is allowed to stir at 0° C. until deemed complete (1 h, monitored by GC/MS). The reaction mixture is then concentrated and purified by column chromatography on silica gel (5% EtOAc/Hex) to afford the desired product (55.3 mg, 0.182 mmol, 91% yield) (7). Analytical data matches that reported in the literature (Lee, J.-E. et al., *Angew. Chem.* 2008, 120, 151, incorporated herein by reference). $^1$H NMR (500 MHz, CDCl$_3$): δ 7.25-7.13 (m, 5H), 4.16-4.05 (m, 2H), 2.88 (dd, J=16.2, 10.0 Hz, 1H), 2.74 (dd, J=10.0, 6.1 Hz, 1H), 2.65 (dd, J=16.3, 6.1 Hz, 1H), 1.22 (s, 6H), 1.17 (s, 6H). Enantiomeric ratio (98:2) is determined after oxidation to the β-hydroxy compound and measured by chiral phase HPLC (chiralcel OD-H; i-PrOH-hexane, 10:90, 0.5 mL/min); (5) isomer t$_r$=18.0 min. and (R) isomer t$_r$=24.4 min. Absolute stereochemistry is assigned by analogy.

Example 19

Ni Catalyzed Reductive Coupling

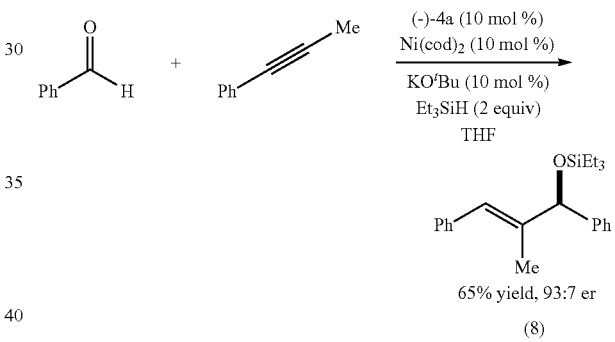

A flame-dried 2 dram vial equipped with a stirbar is brought into the glovebox and charged with (−)-4a (10.7 mg, 0.019 mmol), Ni(COD)$_2$ (a nickel catalyst) (5.20 mg, 0.019 mmol), and KO$^t$Bu (2.12 mg, 0.019 mmol) and then sealed with a screw cap with a Teflon septa. The vial is then taken out of the glovebox and THF (1.5 mL) is added. The solution is allowed to stir for 10 minutes at ambient temperature and then the reaction mixture is cooled to 0° C. Triethylsilane (60.2 uL, 0.377 mmol) is added to the reaction at 0° C. and the solution is stirred for 5 minutes before being warmed back to ambient temperature. Benzaldehyde (19.2 uL, 0.188 mmol) is then added followed by slow addition of a solution of 1-phenyl-1-propyne (30.7 uL, 0.245 mmol) in THF (0.4 mL) over the course of 2 hours. After the addition is complete it is allowed to stir at ambient temperature overnight (12 hours) and then the reaction is quenched by opening to air and stirring for 15 minutes. The crude reaction mixture is then filtered through a plug of silica gel (30% EtOAc/Hex) and the solvent is evaporated under reduced pressure. The crude material is then purified by column chromatography on silica (1-2% EtOAc/Hex) to provide the product (41.5 mg, 0.123 mmol, 65% yield) (8) as a clear oil. Analytical data matches that reported in the literature (Infante, R. et al., *Eur. J. Org. Chem.* 2013, 2013, 4863. $^1$H NMR (500 MHz, CDCl$_3$): δ 7.56 (d, J=7.5 Hz, 2H) 7.41-7.45 (m, 6H) 7.30-7.36 (m, 2H) 6.85 (s, 1H), 5.38 (s, 1H) 1.80 (d, J=1.5 Hz, 3H) 1.09 (t, J=8.5 Hz, 9H) 0.78 (q, J=8.0 Hz, 6H). Enantiomeric ratio (93:7) is determined after silyl deprotection followed by chiral phase HPLC (Regis (S,S)-Whelk-01, 25 cm×4.6 mm; 5% IPA/hexanes 1.0 mL/min, 254 nm), (S) isomer $t_r$=8.1 min. and (R) isomer $t_r$=9.4 min. Absolute stereochemistry is assigned by analogy.

Example 20

Crystal Structure—Determination of Absolute Stereochemistry of (+)-Ferrocenyl Mesityl Imidazolium Tetrafluoroborate (4a)

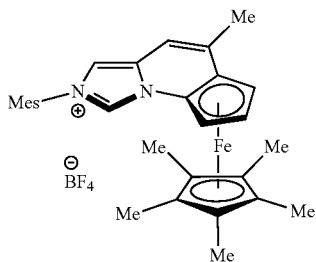

The absolute stereochemistry of (+)-ferrocenyl mesityl imidazolium tetrafluoroborate (4a) is determined by the X-ray diffraction. Recrystallized from solvent diffusion of $Et_2O$ into $CH_2Cl_2$.

X-ray diffraction is performed at 100.03 K and raw frame data is processed using SAINT. Molecular structures are solved using direct methods and refined on F2 by full-matrix least-square techniques. The GOF=1.039 for 352 variables refined to R1=0.0298 for 4427 reflections with I>2α(I). A multi-scan absorption correction is performed and the Flack parameter is −0.0090(19). The crystal is deposited in the Cambridge Crystallographic Data Centre and assigned as CCDC 1007913.

Example 21

Crystal Structure—Determination of Absolute Stereochemistry of (−)-Ferrocenyl Mesityl Imidazolium Copper Chloride Complex

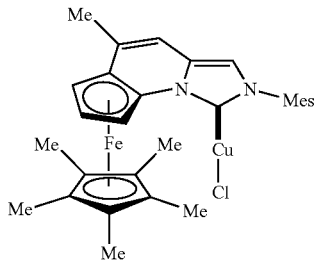

The absolute stereochemistry of (−)-ferrocenyl mesityl imidazolium copper chloride complex is determined by the X-ray diffraction. Recrystallized from slow evaporation of $CH_2Cl_2$/pentane at −30° C.

X-ray diffraction is performed at 100.04 K and raw frame data is processed using SAINT. Molecular structures is solved using direct methods and refined on F2 by full-matrix least-square techniques. The GOF=1.047 for 325 variables refined to R1=0.0201 for 4072 reflections with I>2α(I). A multi-scan absorption correction is performed and the Flack parameter is 0.033(2). Further information can be found in the CIF file. This crystal is deposited in the Cambridge Crystallographic Data Centre and assigned as CCDC 1007914.

In conclusion, a new class of planar chiral N-heterocyclic carbenes (NHCs) which incorporate an iron sandwich complex into the NHC framework have been prepared. Additionally, a survey of organocatalytic and transition metal-catalyzed reactions demonstrates the utility of this new NHC towards catalysis. The late-stage formation of the azolium allows for a modular synthesis of derivatives.

What is claimed is:
1. A catalyst compound selected from a group consisting of

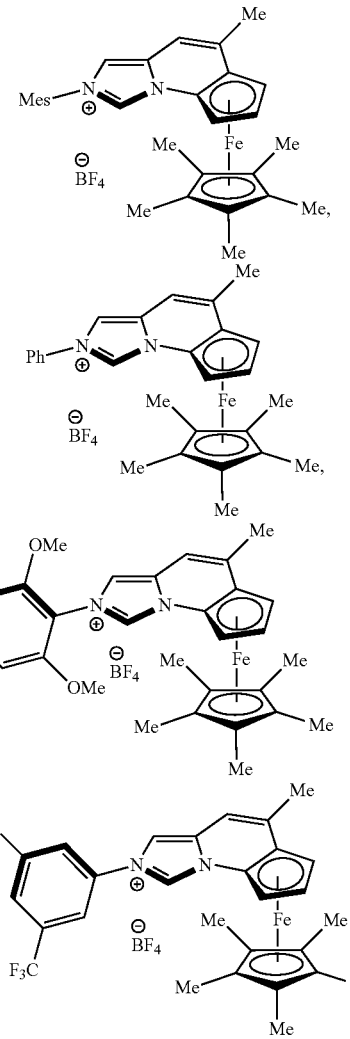

and

2. A method of preparing an addition product of a homoenolate and an α-ketoester comprising contacting the homoenolate and the α-ketoester with a compound of claim 1 and affording an annulation product.

3. A method for nickel-catalyzed reductive coupling of an aldehyde and to an alkyne comprising contacting the aldehyde and the alkyne with a nickel catalyst and a compound of claim 1 and affording an allylic alcohol.

4. A method according to claim 3, wherein the allylic alcohol is formed in an enantiometeric ratio of about 93:7.

5. A method according to claim 3, wherein the allylic alcohol is formed with about 20:1 regioselectivity.

6. A method for copper-catalyzed conjugate borylation of an α,β-unsaturated ester comprising complexing a compound of claim 1 with CuCl to form a catalytic complex, contacting the α,β-unsaturated ester and a boron-containing compounds with the catalytic complex, and affording a conjugate product.

7. A method according to claim 6, wherein the catalytic complex is a complex comprising CuCl and

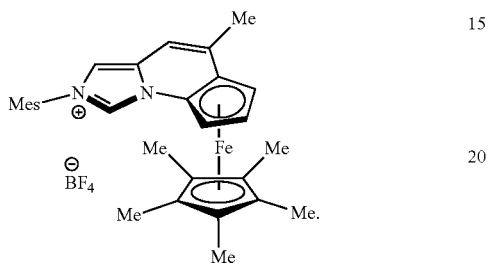

8. A method according to claim 7, wherein the boron-containing compound is bis(pinacolato)diboron.

* * * * *